United States Patent [19]
Noble, Jr.

[11] Patent Number: 5,633,427
[45] Date of Patent: *May 27, 1997

[54] INBRED CORN LINE PHHB

[75] Inventor: Stephen W. Noble, Jr., Johnston, Iowa

[73] Assignee: Pioneer Hi-Bred International, Inc., Des Moines, Iowa

[*] Notice: The term of this patent shall not extend beyond the expiration date of Pat. No. 5,444,178.

[21] Appl. No.: 500,285

[22] Filed: Jul. 10, 1995

Related U.S. Application Data

[63] Continuation of Ser. No. 189,004, Jan. 24, 1994, Pat. No. 5,444,178.

[51] Int. Cl.$^6$ .................. A01H 5/00; A01H 1/00
[52] U.S. Cl. .......... 800/200; 800/250; 800/DIG. 56; 47/58; 47/DIG. 1
[58] Field of Search .................. 800/200, 205, 800/250, DIG. 56; 47/58

[56] References Cited

U.S. PATENT DOCUMENTS 5,444,178   8/1995   Noble, Jr. .................. 800/200

Primary Examiner—Gary Benzion
Attorney, Agent, or Firm—Pioneer Hi-Bred International, Inc.

[57] ABSTRACT

According to the invention, there is provided an inbred corn line, designated PHHB4. This invention thus relates to the plants and seeds of inbred corn line PHHB4 and to methods for producing a corn plant produced by crossing the inbred line PHHB4 with itself or with another corn plant. This invention further relates to hybrid corn seeds and plants produced by crossing the inbred line PHHB4 with another corn line or plant.

2 Claims, 3 Drawing Sheets

INBRED CORN LINE PHHB

REFERENCE TO RELATED APPLICATION

This is a continuation of prior application Ser. No. 08/189,004, filed Jan. 24, 1994, now U.S. Pat. No. 5,444,178.

FIELD OF THE INVENTION

This invention is in the field of corn breeding, specifically relating to an inbred corn line designated PHHB4.

BACKGROUND OF THE INVENTION

Plant Breeding

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Corn plants (*Zea mays* L.) can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the incipient ears.

The development of a hybrid corn variety involves three steps: (1) the selection of plants from various germplasm pools; (2) the selfing of the selected plants for several generations to produce a series of inbred lines, which, although different from each other, breed true and are highly uniform; and (3) crossing the selected inbred lines with unrelated inbred lines to produce the hybrid progeny ($F_1$). During the inbreeding process in corn, the vigor of the lines decreases. Vigor is restored when two unrelated inbred lines are crossed to produce the hybrid progeny. An important consequence of the homozygosity and homogeneity of the inbred lines is that the hybrid between any two inbreds will always be the same. Once the inbreds that give a superior hybrid have been identified, the hybrid seed can be reproduced indefinitely as long as the homogeneity of the inbred parents is maintained.

The objective of commercial maize inbred line development programs is to develop new inbred lines that combine to produce high grain yields and superior agronomic performance in hybrid combination. The primary trait breeders seek is yield. However, other major agronomic traits are of importance in hybrid combination and have an impact on yield or otherwise provide superior performance in hybrid combinations. Such traits include percent grain moisture at harvest, relative maturity, resistance to stalk breakage, resistance to root lodging, grain quality, and disease and insect resistance. In addition the lines per se must have acceptable performance for parental traits such as seed yields, kernel sizes, pollen production, all of which affect ability to provide parental lines in sufficient quantity and quality for hybridization. Traits have been shown to be under genetic control and many if not all of the traits are affected by multiple genes. Thus, to be selected as an inbred line, the inbred must be able to combine such that the desired traits are passed to the hybrid and also be able to satisfy production requirements as a parental line.

Pedigree Breeding

The pedigree method of breeding is the mostly widely used methodology for new inbred line development.

In general terms this procedure consists of crossing two inbred lines to produce the non-segregating $F_1$ generation, and self pollination of the $F_1$ generation to produce the $F_2$ generation that segregates for all factors for which the inbred parents differ. An example of this process is set forth below. Variations of this generalized pedigree method are used, but all these variations produce a segregating generation which contains a range of variation for the traits of interest.

Example 1

Hypothetical Example of Pedigree Breeding Program

Consider a cross between two inbred lines that differ for alleles at five loci.
The parental genotypes are:

| Parent 1 | A b C d e F/A b C d e F |
|---|---|
| Parent 2 | a B c D E f/a B c D E f | the $F_1$ from a cross between these two parents is:

| $F_1$ | A b C d e F/a B c D E f |
|---|---|

Selfing $F_1$ will produce an $F_2$ generation including the following genotypes:

A B c D E f/a b C d e F
A B c D e f/a b C d E F
A B c D e f/a b C d e F
.
.

The number of genotypes in the $F_2$ is $3^6$ for six segregating loci (729) and will produce $(2^6)-2$ possible new inbreds, (62 for six segregating loci).

Each inbred parent which is used in breeding crosses represents a unique combination of genes, and the combined effects of the genes define the performance of the inbred and its performance in hybrid combination. There is published evidence (Smith, O. S., J. S. C. Smith, S. L. Bowen, R. A. Tenborg and S. J. Wall, *TAG* 80:833–840 (1990)) that each of these lines are different and can be uniquely identified on the basis of genetically-controlled molecular markers.

It has been shown (Hallauer, Arnel R. and Miranda, J. B. Fo. *Quantitative Genetics in Maize Breeding*, Iowa State University Press, Ames Iowa (1981)) that most traits of economic value in maize are under the genetic control of multiple genetic loci, and that there are a large number of unique combinations of these genes present in elite maize germplasm. If not, genetic progress using elite inbred lines would no longer be possible. Studies by Duvick and Russell (Duvick, D. N. *Maydica* 37:69–79 (1992); Russell, W. A. *Maydica* XXIX:375–390 (1983)) have shown that over the last 50 years the rate of genetic progress in commercial hybrids has been between 1 and 2% per year.

The number of genes affecting the trait of primary economic importance in maize, grain yield, has been estimated to be in the range of 10–1000. Inbred lines which are used as parents for breeding crosses differ in the number and combination of these genes. These factors make the plant breeder's task more difficult. Compounding this is evidence that no one line contains the favorable allele at all loci, and that different alleles have different economic values depending on the genetic background and field environment in which the hybrid is grown. Fifty years of breeding experience shows that there are many genes affecting grain yield and each of these has a relatively small effect on this trait. The effects are small compared to breeders' ability to measure grain yield differences in evaluation trials. Therefore, the parents of the breeding cross must differ at several of these loci so that the genetic differences in the progeny will be large enough that breeders can develop a line that increases the economic worth of its hybrids over that of hybrids made with either parent.

If the number of loci segregating in a cross between two inbred lines is n, the number of unique genotypes in the $F_2$ generation is $3^n$ (Example 2) and the number of unique inbred lines from this cross is $\{(2^n)-2\}$. Only a very limited number of these combinations are useful. Only about 1 in 10,000 of the progeny from $F_2$'s are commercially useful.

By way of example, if it is assumed that the number of segregating loci in $F_2$ is somewhere between 20 and 50, and that each parent is fixed for half the favorable alleles, it is then possible to calculate approximate probabilities of finding an inbred that has the favorable allele at $\{(n/2)+m\}$ loci, where n/2 is the number of favorable alleles in each of the parents and m is the number of additional favorable alleles in the new inbred. See Example 2 below. The number m is assumed to be greater than three because each allele has so small an effect that evaluation techniques are not sensitive enough to detect differences due to three or less favorable alleles. The probabilities in Example 2 are on the order of $10^{-5}$ or smaller and they are the probabilities that at least one genotype with (n/2)+m favorable alleles will exist.

To put this in perspective the number of plants grown on 60 million acres (approximate U.S. corn acreage) at 25000 plants/acre is $1.5 \times 10^{12}$.

Example 2

Probability of Finding an Inbred with m of n Favorable Alleles

Assume each parent has n/2 of the favorable alleles and only ½ of the combinations of loci are economically useful.

| no. of segregating loci (n) | no. favorable alleles in Parents (n/2) | no. additional favorable alleles in new inbred | Probability that genotype occurs* |
| --- | --- | --- | --- |
| 20 | 10 | 14 | $3 \times 10^{-5}$ |
| 24 | 12 | 16 | $2 \times 10^{-5}$ |
| 28 | 14 | 18 | $1 \times 10^{-5}$ |
| 32 | 16 | 20 | $8 \times 10^{-6}$ |
| 36 | 18 | 22 | $5 \times 10^{-6}$ |
| 40 | 20 | 24 | $3 \times 10^{-6}$ |
| 44 | 22 | 26 | $2 \times 10^{-6}$ |
| 48 | 24 | 28 | $1 \times 10^{-6}$ |

*Probability that a useful combination exists, does not include the probability of identifying this combination if it does exist.

The possibility of having a usably high probability of being able to identify this genotype based on replicated field testing would be most likely smaller than this, and is a function of how large a population of genotypes is tested and how testing resources are allocated in the testing program.

At Pioneer Hi-Bred International, a typical corn research station has a staff of four, and 20 acres of breeding nursery. Those researchers plant those 20 acres with 25,000 nursery rows, 15,000 yield test plots in 10–15 yield test sites, and one or two disease-screening nurseries. Employing a temporary crew of 20 to 30 pollinators, the station makes about 65,000 hand pollinations per growing season. Thus, one of the largest plant breeding programs in the world does not have a sufficiently large breeding population to be able to rely upon "playing the numbers" to obtain successful research results. Nevertheless, Pioneer's breeders at each station produce from three to ten new inbreds which are proposed for commercial use each year. Over the 32 Pioneer research stations in North America, this amounts to from about 100 to 300 new inbreds proposed for use, and less than 50 and more commonly less than 30 of these inbreds that actually satisfy the performance criteria for commercial use.

This is a result of plant breeders using their skills, experience and intuitive ability to select inbreds having the necessary qualities.

SUMMARY OF THE INVENTION

According to the invention, there is provided a novel inbred corn line, designated PHHB4. This invention thus relates to the seeds of inbred corn line PHHB4, to the plants of inbred corn line PHHB4, and to methods for producing a corn plant produced by crossing the inbred line PHHB4 with itself or another corn line. This invention further relates to hybrid corn seeds and plants produced by crossing the inbred line PHHB4 with another corn line.

DEFINITIONS

In the description and examples that follow, a number of terms are used herein. In order to provide a clear and consistent understanding of the specification and claims, including the scope to be given such terms, the following definitions are provided. ABS is in absolute terms and % MN is percent of the mean for the experiments in which the inbred or hybrid was grown.

BAR PLT=BARREN PLANTS. The percent of plants per plot that were not barren (lack ears).

BRT STK=BRITTLE STALKS. This is a measure of the stalk breakage near the time of pollination, and is an indication of whether a hybrid or inbred would snap or break near the time of flowering under severe winds. Data are presented as percentage of plants that did not snap.

BU ACR=YIELD (BUSHELS/ACRE). Actual yield of the grain at harvest in bushels per acre adjusted to 15.5% moisture.

DRP EAR=DROPPED EARS. A measure of the number of dropped ears per plot and represents the percentage of plants that did not drop ears prior to harvest.

EAR HT=EAR HEIGHT. The ear height is a measure from the ground to the highest placed developed ear node attachment and is measured in inches.

EAR SZ=EAR SIZE. A 1 to 9 visual rating of ear size. The higher the rating the larger the ear size.

EST CNT=EARLY STAND COUNT. This is a measure of the stand establishment in the spring and represents the number of plants that emerge on a per plot basis for the inbred or hybrid.

GDU SHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp})}{2} - 50$$

The highest maximum temperature used is 86° F. and the lowest minimum temperature used is 50° F. For each inbred or hybrid it takes a certain number of GDUs to reach various stages of plant development.

GDU SLK=GDU TO SILK. The number of growing degree units required for an inbred line or hybrid to have approximately 50 percent of the plants with silk emergence from time of planting. Growing degree units are calculated by the Barger Method as given in GDU SHD definition.

GRN APP=GRAIN APPEARANCE. This is a 1 to 9 rating for the general appearance of the shelled grain as it is harvested based on such factors as the color of the harvested grain, any mold on the grain, and any cracked grain. High scores indicate good grain quality.

MST=HARVEST MOISTURE. The moisture is the actual percentage moisture of the grain at harvest.

PLT HT=PLANT HEIGHT. This is a measure of the height of the plant from the ground to the tip of the tassel in inches.

POL SC=POLLEN SCORE. A 1 to 9 visual rating indicating the amount of pollen shed. The higher the score the more pollen shed.

POL WT=POLLEN WEIGHT. This is calculated by dry weight of tassels collected as shedding commences minus dry weight from similar tassels harvested after shedding is complete.

It should be understood that the inbred can, through routine manipulation of cytoplasmic factors, be produced in a cytoplasmic male-sterile form which is otherwise phenotypically identical to the male-fertile form.

PRM=PREDICTED RM. This trait, predicted relative maturity (RM), is based on the harvest moisture of the grain. The relative maturity rating is based on a known set of checks and utilizes standard linear regression analyses and is referred to as the Comparative Relative Maturity Rating System which is similar to the Minnesota Relative Maturity Rating System.

RT LDG=ROOT LODGING. Root lodging is the percentage of plants that do not root lodge; plants that lean from the vertical axis at an approximately 30° angle or greater would be counted as root lodged.

SCT GRN=SCATTER GRAIN. A 1 to 9 visual rating indicating the amount of scatter grain (lack of pollination or kernel abortion) on the ear. The higher the score the less scatter grain.

SDG VGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A corn breeder may utilize his or her own set of traits for the selection index. One of the traits that is almost always included is yield. The selection index data presented in the tables represent the mean value averaged across testing stations.

STA GRN=STAY GREEN. Stay green is the measure of plant health near the time of black layer formation (physiological maturity). A high score indicates better late-season plant health.

STK CNT=NUMBER OF PLANTS. This is the final stand or number of plants per plot.

STK LDG=STALK LODGING. This is the percentage of plants that did not stalk lodge (stalk breakage) as measured by either natural lodging or pushing the stalks and determining the percentage of plants that break below the ear.

TAS BLS =TASSEL BLAST. A 1 to 9 visual rating was used to measure the degree of blasting (necrosis due to heat stress) of the tassel at time of flowering. A 1 would indicate a very high level of blasting at time of flowering, while a 9 would have no tassel blasting.

TAS SZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEX EAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data is given as percentage of tillers: number of tillers per plot divided by number of plants per plot.

TST WT=TEST WEIGHT (UNADJUSTED). The measure of the weight of the grain in pounds for a given volume (bushel).

TST WTA=TEST WEIGHT ADJUSTED. The measure of the weight of the grain in pounds for a given volume (bushel) adjusted for percent moisture.

YLD=YIELD. It is the same as BU ACR ABS.

YLD SC=YIELD SCORE. A 1 to 9 visual rating was used to give a relative rating for yield based on plot ear piles. The higher the rating the greater visual yield appearance.

MDM CPX=Maize Dwarf Mosaic Complex (MDMV= Maize Dwarf Mosaic Virus & MCDV=Maize Chlorotic Dwarf Virus): Visual rating (1–9 score) where a "1" is very susceptible and a "9" is very resistant.

SLF BLT=Southern Leaf Blight (*Bipolaris maydis, Helminthosporium maydis*): Visual rating (1–9 score) where a "1" is very susceptible and a "9" is very resistant.

NLF BLT=Northern Leaf Blight (*Exserohilum turcicum, H. turcicum*): Visual rating (1–9 score) where a "1" is very susceptible and a "9" is very resistant.

COM RST=Common Rust (*Puccinia sorghi*): Visual rating (1–9 score) where a "1" is very susceptible and a "9" is very resistant.

GLF SPT=Gray Leaf Spot (*Cercospora zeae-maydis*): Visual rating (1–9 score) where a "1" is very susceptible and a "9" is very resistant.

STW WLT=Stewart's Wilt (*Erwinia stewartii*): Visual rating (1–9 score) where a "1" is very susceptible and a "9" is very resistant.

HD SMT=Head Smut (*Sphacelotheca reiliana*): Percentage of plants that did not have infection.

EAR MLD=General Ear Mold: Visual rating (1–9 score) where a "1" is very susceptible and a "9" is very resistant. This is based on overall rating for ear mold of mature ears without determining specific mold organism, and may not be predictive for a specific ear mold.

ECB DPE=Dropped ears due to European Corn Borer (*Ostrinia nubilalis*): Percentage of plants that did not drop ears under second brood corn borer infestation.

ECB 2SC=European Corn Borer Second Brood (*Ostrinia nubilalis*): Visual rating (1–9 score) of post flowering damage due to infestation by European Corn Borer. A "1" is very susceptible and a "9" is very resistant.

ECB 1LF=European Corn Borer First Brood (*Ostrinia nubilalis*): Visual rating (1–9 score) of pre-flowering leaf feeding by European Corn Borer. A "1" is very susceptible and a "9" is very resistant.

DETAILED DESCRIPTION OF THE INVENTION

Figure 1:
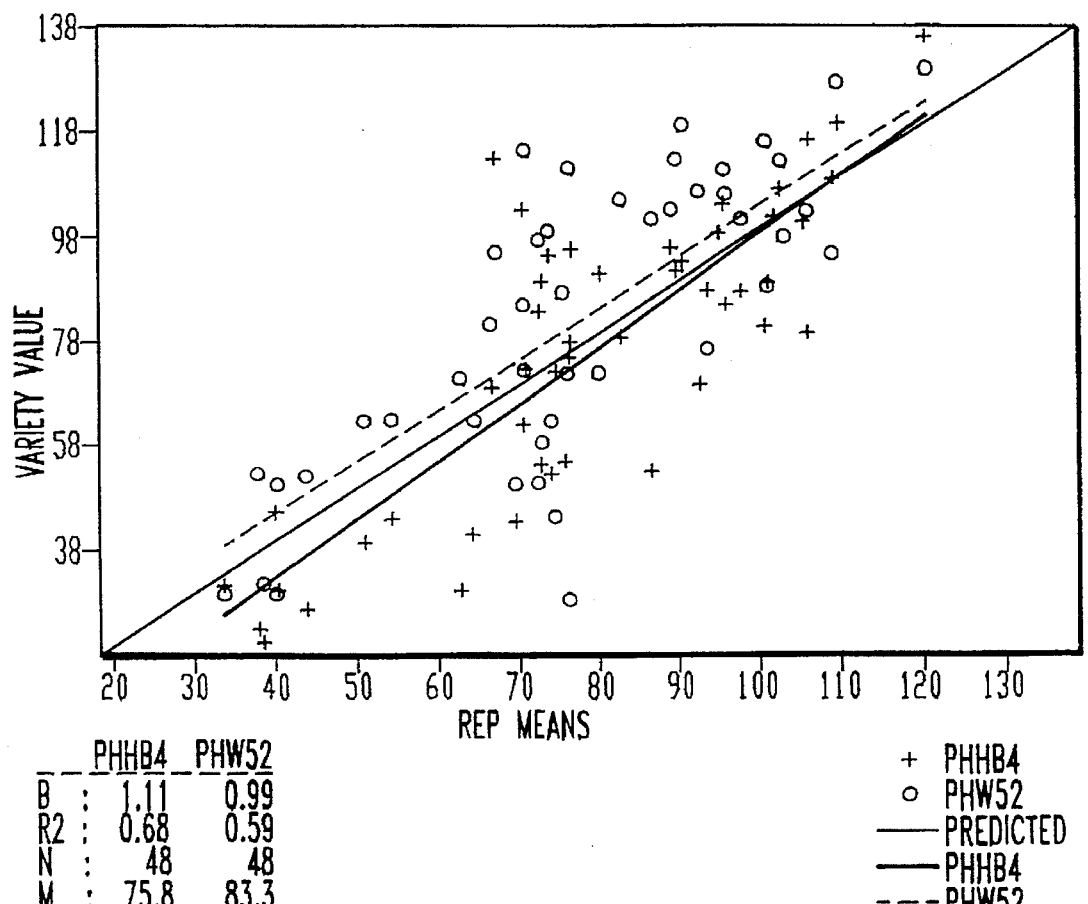
FIGS. 1–3 show data for the trait Bushels Per Acre. The results of FIGS. 1–3 compare PHHB4 to PHW52, PHP38, and PHR61, respectively.

PHHB4 brings together more yield in hybrids than either parental line. In hybrid combination PHHB4 has desirable plant and ear height, resistance to brittle stalk, and resistance to common rust. Hybrids of PHHB4 do well in both dry and wet years compared to the closest prior art, but are especially better in wet years.

Inbred corn line PHHB4 is a yellow, dent corn inbred and provides an acceptable female parental line in crosses for producing first generation F1 corn hybrids. PHHB4 is adapted to most regions of the United States but does best in Nebraska, Iowa, Illinois and Indiana.

The inbred has shown uniformity and stability within the limits of environmental influence for all the traits as described in the Variety Description Information (Table 1) that follows. Most of the data in the Variety Description information was collected at Johnston, Iowa. The inbred has been self-pollinated and ear-rowed a sufficient number of generations with careful attention paid to uniformity of plant type to ensure homozygosity and phenotypic stability. The line has been increased both by hand and in isolated fields with continued observation for uniformity. No variant traits have been observed or are expected in PHHB4.

Inbred corn line PHHB4, being substantially homozygous, can be reproduced by planting seeds of the line, growing the resulting corn plants under self-pollinating or sib-pollinating conditions with adequate isolation, and harvesting the resulting seed, using techniques familiar to the agricultural arts.

TABLE 1

VARIETY DESCRIPTION INFORMATION
INBRED = PHHB4
Type: Dent    Region Best Adapted: Most Regions A.  Maturity: Average across maturity zones. Zone: 0
    Heat Unit Shed: 1510
    Heat Unit Silk: 1540
    No. Reps: 50

$$\text{HEAT UNITS} = \frac{[\text{Max. Temp.} (° < \_86° \text{ F.}) + \text{Min. Temp} (>\_50° \text{ F.})]^*}{2} - 50$$

*If maximum is greater than 86 degrees fahrenheit, then 86 is used and if minimum is less than 50, then 50 is used. Heat units accumulated daily and can not be less than 0.

B. Plant Characteristics
  Plant height (to tassel tip): 227 cm
  Length of top ear internode: 11 cm
  Number of ears per stalk: Single
  Ear height (to base of top ear): 69 cm
  Number of tillers: None
  Cytoplasm type: Normal
C. Leaf
  Color: (WF9) Medium Green
  Angle from Stalk: 30–60 degrees
  Marginal Waves: (HY) None
  Number of Leaves (mature plants): 21
  Sheath Pubescence: (W22) Light
  Longitudinal Creases: (OH56A) Few
  Length (Ear node leaf): 73 cm
  Width (widest point, ear node leaf): 9 cm
D. Tassel
  Number lateral branches: 1
  Branch Angle from central spike: >45 degrees
  Pollen Shed: Light based on Pollen Yield Test (26% of experiment means)
  Peduncle Length (top leaf to basal branches): 19 cm
  Anther Color: Pink
  Glume Color: Green
E. Ear (Husked Ear Data Except When Stated Otherwise)
  Length: 16 cm
  Weight: 151 gm
  Mid-point Diameter: 48 mm
  Silk Color: Green
  Husk Extension (Harvest stage): Medium (barely covering ear)
  Taper of Ear: Slight
  Position of Shank (dry husks): Upright
  Kernel Rows: Straight, Distinct Number=14
  Husk Color (fresh): Light Green
  Husk Color (dry): Buff
  Shank Length: 11 cm
  Shank (No. of internodes): 8
F. Kernel (Dried)
  Size (from ear mid-point)
  Length: 12 mm
  Width: 9 mm
  Thick: 5 mm
  Shape Grade (% rounds): 40–60 (42% medium round based on Parent Test Data)
  Pericarp Color: Colorless
  Aleurone Color: Homozygous Yellow
  Endosperm Color: Yellow
  Endosperm Type: Normal Starch
  Gm Wt/100 Seeds (unsized): 37 gm
G. Cob
  Diameter at mid-point: 27 mm
  Strength: Strong
  Color: Red
H. Diseases
  Corn Lethal Necrosis (MCMV=Maize Chlorotic Mottle Virus and MDMV=Maize Dwarf Mosaic Virus): Intermediate
  Maize Dwarf Mosaic Complex (MDMV & MCDV= Maize Dwarf Virus): Susceptible
  Anthracnose Stalk Rot ((*C. graminicola*): Intermediate
  S. Leaf Blight (*B. maydis*): Resistant
  Carbonum Leaf Blight (*H. carbonum*): Intermediate
  N. Leaf Blight (*E. turcicum*): Intermediate
  Common Rust (*P. sorghi*): Resistant
  Gray Leaf Spot (*C. zeae*): Susceptible Stewart's Wilt (*E. stewartii*): Resistant Common Smut (*U. maydis*): Highly Resistant Head Smut (*S. reiliana*): Highly Resistant Fusarium Ear Mold (*F. moniliforme*): Intermediate Gibberella Ear Rot (*G. zeae*): Intermediate I. Insects European Corn Borer-1 Leaf Damage (Pre-flowering): Susceptible European Corn Borer-2 (Post-flowering): Susceptible The above descriptions are based on a scale of 1–9, 1 being highly susceptible, 9 being highly resistant.

S (Susceptible): Would generally represent a score of 1–3.

I (Intermediate): Would generally represent a score of 4–5.

R (Resistant): Would generally represent a score of 6–7.

H (Highly Resistant): Would generally represent a score of 8–9. Highly resistant does not imply the inbred isimmune.

| J. Variety Most Closely Resembling: | |
|---|---|
| Character | Inbred |
| Maturity | PHW52 |
| Usage | PHW52 |

PHW52(PVP Certificate No. 8800215) is a Pioneer Hi-Bred International, Inc. proprietary inbred.

Data for Items B, C, D, E, F, and G is based primarily on a maximum of two reps from Johnston, Iowa grown in 1992, plus description information from the maintaining station.

ELECTROPHORESIS RESULTS

Isozyme Genotypes for PHHB4

Isozyme data were generated for inbred corn line PHHB4 according to the procedures described in Stuber, C. W., Wendel, J. F., Goodman, M. M., and Smith, J. S. C., "Techniques and Scoring Procedures for Starch Gel Electrophoresis of Enzymes from Maize (*Zea mays* L.)", Technical Bulletin No. 286, North Carolina Agricultural Research Service, North Carolina State University, Raleigh, N.C. (1988).

The data in Table 2 compares PHHB4 with its parents, PHW52 and PHV94.

TABLE 2

ELECTROPHORESIS RESULTS FOR PHHB4 AND ITS PARENTS PHW52 AND PHV94

| LOCI | PHHB4 | PARENTS | |
|---|---|---|---|
| | | PHW52 | PHV94 |
| ACP1 | 2 | 2 | 4 |
| ADH1 | 4 | 4 | 4 |
| CAT3 | 9 | 9 | 9 |
| DIA1 | 8 | 8 | 8 |
| GOT1 | 4 | 4 | 4 |
| GOT2 | 2 | 2 | 4 |
| GOT3 | 4 | 4 | 4 |
| IDH1 | 4 | 4 | 4 |
| IDH2 | 6 | 6 | 6 |
| MDH1 | 6 | 6 | 6 |
| MDH2 | 6 | 6 | 6 |
| MDH3 | 16 | 16 | 16 |
| MDH4 | 12 | 12 | 12 |

TABLE 2-continued

ELECTROPHORESIS RESULTS FOR PHHB4 AND ITS PARENTS PHW52 AND PHV94

| LOCI | PHHB4 | PARENTS | |
|---|---|---|---|
| | | PHW52 | PHV94 |
| MDH5 | 12 | 12 | 12 |
| MMM | 4 | 4 | 4 |
| PGM1 | 9 | 9 | 9 |
| PGM2 | 4 | 4 | 4 |
| PGD1 | 2 | 2 | 2 |
| PGD2 | 5 | 5 | 5 |
| PHI1 | 4 | 5 | 4 |

Examples

INBRED AND HYBRID PERFORMANCE OF PHHB4

In the examples that follow, the traits and characteristics of inbred corn line PHHB4 are given as a line in comparison with other inbreds and in hybrid combination. The data collected on inbred corn line PHHB4 is presented for the key characteristics and traits.

Table 3A compares PHHB4 to PHW52. PHHB4 has lower yield and grain harvest moisture but higher test weight than PHW52. PHHB4 is a taller inbred with higher ear placement compared to PHW52. PHHB4 has better seedling vigor and sheds (GDU Shed) later than PHW52. PHHB4 has good ear texture but more scattergrain compared to PHW52. PHHB4 has better resistance to Stewart's wilt and first brood European corn borer than PHW52.

The data in Table 3B shows PHHB4 and PHP38 have similar yield and test weight but PHHB4 has lower grain harvest moisture. PHHB4 has a larger ear and is taller with lower ear placement PHP38. PHHB4 flowers (GDU Shed and GDU Silk) later than PHP38. PHHB4 has better Stewart's wilt resistance than PHP38.

Table 3C compares PHHB4 to PHR61. The data shows PHHB4 has higher yield and lower test weight than PHR61. PHHB4 has a larger ear and is a shorter inbred with lower ear placement than PHR61. PHHB4 flowers later (GDU Shed and GDU Silk) than PHR61. PHHB4 has better staygreen than PHR61.

Table 4A compares PHHB4 to PHW52 when both were crossed to the same inbred testers. The PHHB4 hybrids have higher yield and test weight but lower grain harvest moisture compared to the PHW52 hybrids. The hybrids have similar ear placement but the PHHB4 hybrids are taller.

Table 4B compares PHHB4 to PHP38 when both were crossed to the same inbred testers. The PHHB4 hybrids have higher yield than the PHP38 hybrids. The PHHB4 hybrids shed (GDU Shed) later than the PHP38 hybrids.

Table 4C compares PHHB4 to PHR61 when both were crossed to the same inbred testers. The PHHB4 hybrids have higher yield and grain harvest moisture compared to the PHR61 hybrids. The PHHB4 hybrids shed (GDU Shed) later than the PHR61 hybrids. The PHHB4 hybrids have better grain appearance and are taller with lower ear placement compared to the PHR61 hybrids.

Table 5A compares PHHB4 to PHW52 when both were crossed to the same inbred. The data shows the PHHB4 hybrid is higher yielding with lower grain harvest moisture compared to the PHW52 hybrid. The PHHB4 hybrid has better test weight and grain appearance than the PHW52 hybrid. The PHHB4 hybrid is taller with higher ear placement and sheds (GDU Shed) later than the PHW52 hybrid.

Table 5B compares PHHB4 to PHR61 when both were crossed to the same inbred. The PHHB4 hybrid has higher yield and grain harvest moisture compared to the PHR61 hybrid. The hybrids have similar plant height but the PHHB4 hybrid has lower ear placement than the PHR61 hybrid. The PHHB4 hybrid sheds (GDU Shed) later than the PHR61 hybrid.

BRIEF DESCRIPTION OF THE DRAWINGS

FIG. 1 compares the yield of PHHB4 to PHW52. PHHB4 is lower yielding than PHW52 and has below average yield in low yield environments.

Figure 2:
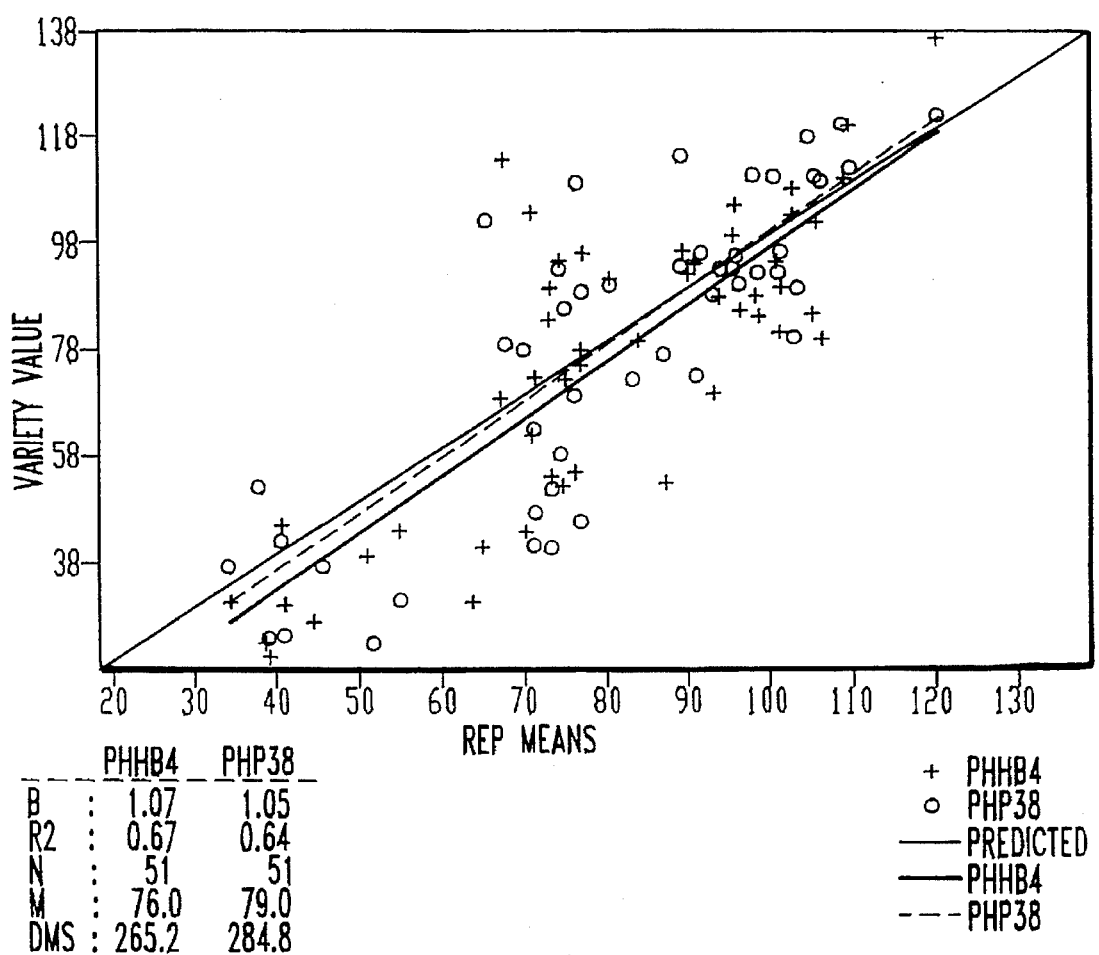

FIG. 2 compares the yield of PHHB4 and PHP38. PHHB4 has lower yield across all environments compared to PHP38.

Figure 3:
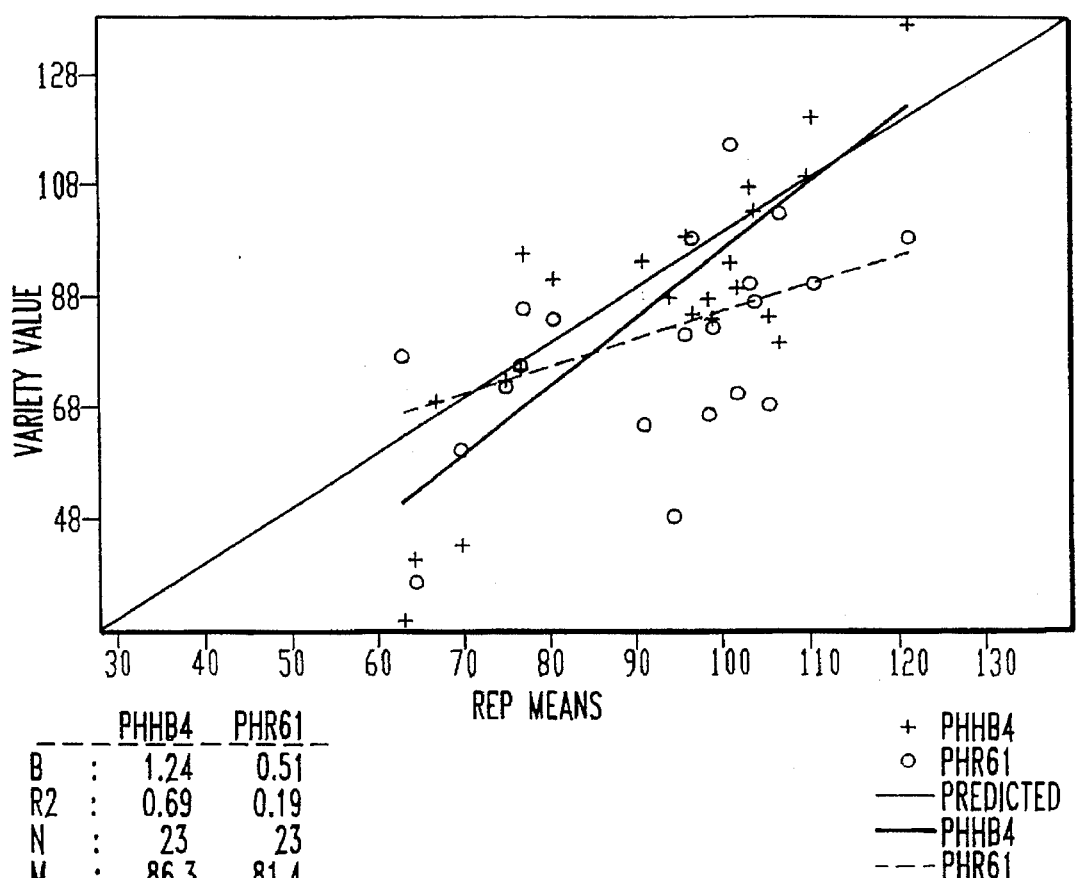

FIG. 3 compares the yield of PHHB4 and PHR61. PHHB4 has below average yield except in the most extreme high yield environments. Compared to PHR61, PHHB4 is higher yielding in high yield environments but lower yielding in low yield environments.

TABLE 3A

PAIRED INBRED COMPARISON DATA
VARIETY #1 - PHHB4
VARIETY #2 - PHW52

| DEPT | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | DRP EAR ABS | TIL LER ABS | GDU SHD ABS | GDU SLK ABS | POL SC ABS |
|---|---|---|---|---|---|---|---|---|---|---|---|---|---|---|---|---|
| TO- | 1 | 76.3 | 96 | 5.5 | 17.9 | 5.8 | 92.0 | 84.5 | 28.3 | 5.5 | 37.3 | 99.5 | 0.8 | 1451 | 1480 | 2.4 |
| TAL | 2 | 82.9 | 106 | 6.3 | 21.2 | 5.8 | 93.9 | 75.6 | 26.3 | 4.9 | 39.7 | 99.9 | 0.9 | 1441 | 1479 | 6.2 |
| SUM | LOCS | 30 | 30 | 19 | 43 | 17 | 57 | 53 | 53 | 55 | 78 | 8 | 54 | 55 | 52 | 18 |
|  | REPS | 78 | 78 | 20 | 92 | 17 | 90 | 92 | 88 | 82 | 145 | 16 | 80 | 65 | 57 | 20 |
|  | DIFF | 6.6 | 10 | 0.8 | 3.4 | 0.1 | 1.9 | 8.9 | 2.1 | 0.6 | 2.3 | 0.4 | 0.2 | 10 | 01 | 3.8 |
|  | PROB | .098* | .093* | .028+ | .000# | .842 | .204 | .000# | .000# | .003# | .000# | .209 | .599 | 0.55* | .922 | .000# |

| DEPT | VAR # | TAS BLS ABS | TAS SZ ABS | TEX EAR ABS | TST WT ABS | GRN APP ABS | SCT GRN ABS | STA GRN ABS | STK LDG ABS | RT LDG ABS | EAR MLD ABS | NLF BLT ABS | STW WLT ABS | ECB 1LF ABS | ECB 2SC ABS |
|---|---|---|---|---|---|---|---|---|---|---|---|---|---|---|---|
| TOTAL | 1 | 9.0 | 2.8 | 6.6 | 58.8 | 6.1 | 5.6 | 5.2 | 94.8 | 98.2 | 7.4 | 4.3 | 5.8 | 3.8 | 4.6 |
| SUM | 2 | 9.0 | 6.0 | 5.9 | 57.0 | 5.6 | 6.8 | 5.7 | 89.0 | 98.1 | 7.5 | 3.9 | 4.0 | 3.1 | 4.1 |
|  | LOCS | 1 | 21 | 14 | 28 | 14 | 19 | 32 | 23 | 14 | 16 | 13 | 4 | 19 | 8 |
|  | REPS | 1 | 23 | 14 | 72 | 27 | 20 | 53 | 51 | 25 | 17 | 20 | 4 | 24 | 14 |
|  | DIFF | 0.0 | 3.2 | 0.7 | 1.8 | 0.5 | 1.2 | 0.5 | 5.8 | 0.1 | 0.1 | 0.4 | 1.8 | 0.7 | 0.4 |
|  | PROB |  | .000# | .035+ | .000# | .312 | .017+ | .153 | .012+ | .883 | .872 | .293 | .006# | .062* | .514 |

\* = 10% SIG
+ = 5% SIG
# = 1% SIG

TABLE 3B

PAIRED INBRED COMPARISON DATA
VARIETY #1 - PHHB4
VARIETY #2 - PHP38

| DEPT | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | DRP EAR ABS | TIL LER ABS | GDU SHD ABS | GDU SLK ABS | POL SC ABS |
|---|---|---|---|---|---|---|---|---|---|---|---|---|---|---|---|---|
| TO- | 1 | 75.3 | 95 | 5.4 | 17.5 | 5.8 | 92.2 | 84.5 | 28.3 | 5.5 | 37.8 | 99.5 | 0.7 | 1450 | 1479 | 2.5 |
| TAL | 2 | 77.1 | 99 | 5.3 | 18.7 | 5.2 | 91.6 | 81.2 | 29.3 | 5.8 | 40.0 | 99.2 | 1.1 | 1426 | 1440 | 5.4 |
| SUM | LOCS | 33 | 33 | 20 | 47 | 17 | 60 | 53 | 53 | 55 | 83 | 8 | 58 | 60 | 57 | 22 |
|  | REPS | 66 | 66 | 21 | 80 | 19 | 81 | 81 | 81 | 75 | 132 | 16 | 79 | 68 | 62 | 24 |
|  | DIFF | 1.8 | 4 | 0.1 | 1.2 | 0.6 | 0.6 | 3.3 | 1.0 | 0.3 | 2.1 | 0.3 | 0.3 | 24 | 39 | 2.9 |
|  | PROB | .599 | .487 | .785 | .000# | .096* | .657 | .000# | .050* | .113 | .002# | .406 | .325 | .000# | .000# | .000# |

| DEPT | VAR # | TAS BLS ABS | TAS SZ ABS | TEX EAR ABS | TST WT ABS | GRN APP ABS | SCT GRN ABS | STA GRN ABS | STK LDG ABS | RT LDG ABS | EAR MLD ABS | NLF BLT ABS | STW WLT ABS | ECB 1LF ABS | ECB 2SC ABS |
|---|---|---|---|---|---|---|---|---|---|---|---|---|---|---|---|
| TOTAL | 1 | 9.0 | 2.8 | 6.6 | 58.6 | 6.1 | 5.7 | 5.2 | 94.8 | 98.2 | 7.4 | 4.3 | 5.8 | 3.9 | 5.0 |
| SUM | 2 | 9.0 | 5.2 | 6.9 | 58.8 | 6.6 | 6.0 | 5.8 | 93.7 | 99.1 | 8.0 | 4.2 | 3.8 | 3.5 | 4.9 |
|  | LOCS | 1 | 22 | 14 | 31 | 15 | 20 | 32 | 23 | 14 | 16 | 13 | 4 | 20 | 7 |
|  | REPS | 1 | 24 | 14 | 62 | 29 | 21 | 48 | 44 | 25 | 17 | 20 | 4 | 25 | 11 |
|  | DIFF | 0.0 | 2.4 | 0.3 | 0.2 | 0.5 | 0.3 | 0.7 | 1.0 | 0.8 | 0.6 | 0.0 | 2.0 | 0.4 | 0.1 |
|  | PROB |  | .000# | .414 | .463 | .056* | .406 | .096* | .136 | .444 | .132 | .886 | .000# | .159 | .818 |

\* = 10% SIG
+ = 5% SIG
# = 1% SIG

TABLE 3C

PAIRED INBRED COMPARISON DATA
VARIETY #1 - PHHB4
VARIETY #2 - PHR61

| DEPT | VAR # | BU ACR ABS | BU ACR % MN | YLD SC ABS | MST ABS | EAR SZ ABS | BAR PLT ABS | PLT HT ABS | EAR HT ABS | SDG VGR ABS | EST CNT ABS | DRP EAR ABS | TIL LER ABS | GDU SHD ABS | GDU SLK ABS | POL SC ABS |
|---|---|---|---|---|---|---|---|---|---|---|---|---|---|---|---|---|
| TO- | 1 | 84.2 | 98 | 5.4 | 17.4 | 5.5 | 92.8 | 86.6 | 28.5 | 5.3 | 34.6 | 100.0 | 0.8 | 1439 | 1470 | 2.4 |
| TAL | 2 | 77.0 | 92 | 5.1 | 17.0 | 4.7 | 91.8 | 91.2 | 32.7 | 5.6 | 39.1 | 100.0 | 1.1 | 1420 | 1431 | 2.5 |
| SUM | LOCS | 17 | 17 | 14 | 31 | 12 | 43 | 33 | 33 | 38 | 60 | 2 | 42 | 47 | 46 | 17 |
|  | REPS | 34 | 34 | 15 | 48 | 12 | 54 | 49 | 49 | 48 | 96 | 4 | 53 | 52 | 50 | 19 |
|  | DIFF | 7.2 | 6 | 0.2 | 0.4 | 0.8 | 1.1 | 4.7 | 4.2 | 0.3 | 4.6 | 0.0 | 0.3 | 19 | 39 | 0.1 |
|  | PROB | .119 | .310 | .701 | .138 | .096* | .608 | .000# | .000# | .159 | .000# | 1.00 | .447 | .003# | .000# | .835 |

| DEPT | VAR # | TAS BLS ABS | TAS SZ ABS | TEX EAR ABS | TST WT ABS | GRN APP ABS | SCT GRN ABS | STA GRN ABS | STK LDG ABS | RT LDG ABS | EAR MLD ABS | NLF BLT ABS | STW WLT ABS | ECB 1LF ABS | ECB 2SC ABS |
|---|---|---|---|---|---|---|---|---|---|---|---|---|---|---|---|
| TOTAL | 1 | 9.0 | 2.7 | 6.7 | 57.1 | 5.6 | 5.4 | 5.5 | 94.4 | 98.4 | 8.0 | 4.3 | 5.7 | 3.6 | 3.7 |
| SUM | 2 | 9.0 | 1.8 | 7.3 | 59.0 | 6.6 | 6.7 | 4.1 | 91.8 | 77.1 | 8.1 | 5.3 | 3.3 | 3.7 | 5.7 |
|  | LOCS | 1 | 14 | 10 | 15 | 8 | 15 | 18 | 11 | 4 | 12 | 11 | 3 | 14 | 3 |
|  | REPS | 1 | 16 | 10 | 30 | 15 | 16 | 26 | 21 | 7 | 13 | 16 | 3 | 17 | 3 |
|  | DIFF | 0.0 | 0.9 | 0.6 | 2.0 | 0.9 | 1.3 | 1.4 | 2.5 | 21.3 | 0.1 | 1.0 | 2.3 | 0.1 | 2.0 |
|  | PROB |  | .017+ | .051* | .000# | .059* | .014+ | .009# | .597 | .405 | .838 | .026+ | .222 | .753 | .074* |

\* = 10% SIG
+ = 5% SIG
# = 1% SIG

TABLE 4A

AVERAGE INBRED BY TESTER PERFORMANCE COMPARING PHW52 TO PHHB4
CROSSED TO THE SAME INBRED TESTERS AND GROWN IN THE SAME
EXPERIMENTS. ALL VALUES ARE EXPRESSED AS PERCENT OF THE EXPERIMENT
MEAN EXCEPT PREDICTED RM, SELECTION INDEX, AND YIELD (BU/ACR).

|  | INBRED | PRM | SEL IND | BU ACR | YLD | MST | GDU SHD | PRM SHD | STK LDG | RT LDG | STA GRN |
|---|---|---|---|---|---|---|---|---|---|---|---|
| TOTAL | REPLIC. |  | 65 | 64 | 64 | 64 | 65 | 21 | 8 | 53 | 17 | 29 |
| MEAN WTS | PHW52 | 112 | 95 | 181 | 98 | 104 | 99 | 108 | 101 | 102 | 106 |
| MEAN WTS | PHHB4 | 110 | 103 | 188 | 101 | 99 | 99 | 108 | 100 | 93 | 100 |
|  | DIFF. | 2 | 9 | 7 | 4 | 5 | 0 | 0 | 1 | 9 | 6 |

|  | INBRED | TST WTA | GRN APP | SDG VGR | EST CNT | STK CNT | PLT HT | EAR HT | DRP EAR | BRT STK |
|---|---|---|---|---|---|---|---|---|---|---|
| TOTAL | REPLIC. | 49 | 23 | 39 | 34 | 65 | 36 | 36 | 10 | 7 |
| MEAN WTS | PHW52 | 100 | 95 | 100 | 101 | 100 | 97 | 96 | 100 | 100 |
| MEAN WTS | PHHB4 | 102 | 99 | 107 | 100 | 102 | 100 | 96 | 100 | 102 |
|  | DIFF. | 1 | 4 | 7 | 1 | 1 | 2 | 0 | 0 | 2 |

TABLE 4B

AVERAGE INBRED BY TESTER PERFORMANCE COMPARING PHP38 TO PHHB4
CROSSED TO THE SAME INBRED TESTERS AND GROWN IN THE SAME
EXPERIMENTS. ALL VALUES ARE EXPRESSED AS PERCENT OF THE EXPERIMENT
MEAN EXCEPT PREDICTED RM, SELECTION INDEX, AND YIELD (BU/ACR).

|  | INBRED | PRM | SEL IND | BU ACR | YLD | MST | GDU SHD | PRM SHD | STK LDG | RT LDG | STA GRN |
|---|---|---|---|---|---|---|---|---|---|---|---|
| TOTAL | REPLIC. | 132 | 137 | 137 | 137 | 140 | 50 | 12 | 113 | 46 | 55 |
| MEAN WTS | PHP38 | 110 | 97 | 178 | 98 | 99 | 99 | 109 | 102 | 102 | 110 |
| MEAN WTS | PHHB4 | 111 | 104 | 185 | 102 | 99 | 101 | 111 | 100 | 100 | 109 |
|  | DIFF. |  | 6 | 7 | 3 | 1 | 2 | 2 | 2 | 2 | 1 |

TABLE 4B-continued

AVERAGE INBRED BY TESTER PERFORMANCE COMPARING PHP38 TO PHHB4 CROSSED TO THE SAME INBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/ACR).

|  | INBRED | TST WTA | GRN APP | SDG VGR | EST CNT | STK CNT | PLT HT | EAR HT | DRP EAR | BRT STK |
|---|---|---|---|---|---|---|---|---|---|---|
| TOTAL | REPLIC. | 115 | 54 | 69 | 73 | 147 | 82 | 82 | 37 | 20 |
| MEAN WTS | PHP38 | 101 | 105 | 105 | 99 | 100 | 96 | 96 | 100 | 102 |
| MEAN WTS | PHHB4 | 101 | 99 | 104 | 98 | 99 | 101 | 95 | 100 | 102 |
|  | DIFF. | 1 | 6 | 1 | 2 | 1 | 4 | 1 | 0 | 0 |

TABLE 4C

AVERAGE INBRED BY TESTER PERFORMANCE COMPARING PHR61 TO PHHB4 CROSSED TO THE SAME INBRED TESTERS AND GROWN IN THE SAME EXPERIMENTS. ALL VALUES ARE EXPRESSED AS PERCENT OF THE EXPERIMENT MEAN EXCEPT PREDICTED RM, SELECTION INDEX, AND YIELD (BU/ACR).

|  | INBRED | PRM | SEL IND | BU ACR | YLD | MST | GDU SHD | PRM SHD | STK LDG | RT LDG | STA GRN |
|---|---|---|---|---|---|---|---|---|---|---|---|
| TOTAL | REPLIC. | 20 | 20 | 20 | 20 | 20 | 10 | 2 | 16 | 8 | 10 |
| MEAN WTS | PHR61 | 106 | 86 | 164 | 92 | 95 | 99 | 109 | 100 | 90 | 107 |
| MEAN WTS | PHHB4 | 108 | 102 | 182 | 102 | 103 | 101 | 110 | 99 | 109 | 108 |
|  | DIFF. | 2 | 16 | 18 | 10 | 8 | 1 | 1 | 1 | 19 | 1 |

|  | INBRED | TST WTA | GRN APP | SDG VGR | EST CNT | STK CNT | PLT HT | EAR HT | BRT STK |
|---|---|---|---|---|---|---|---|---|---|
| TOTAL | REPLIC. | 18 | 10 | 8 | 7 | 22 | 10 | 10 | 2 |
| MEAN WTS | PHR61 | 103 | 109 | 90 | 100 | 102 | 101 | 100 | 106 |
| MEAN WTS | PHHB4 | 102 | 113 | 99 | 96 | 100 | 104 | 98 | 105 |
|  | DIFF. | 1 | 4 | 9 | 4 | 2 | 2 | 2 | 1 |

TABLE 5A

VARIETY #1 - PHHB4 HYBRID
VARIETY #2 - PHW52 HYBRID

| DEPT | VAR # | PRM | PRM SHD | BU ACR ABS | BU ACR % MN | MST % MN | STK LDG % MN | RT LDG % MN | STA GRN % MN | TST WTA % MN |
|---|---|---|---|---|---|---|---|---|---|---|
| TOTAL SUM | 1 | 107 | 109 | 178.8 | 105 | 96 | 98 | 100 | 88 | 100 |
|  | 2 | 109 | 107 | 172.1 | 102 | 101 | 99 | 104 | 105 | 99 |
|  | LOCS | 30 | 18 | 133 | 133 | 136 | 115 | 53 | 55 | 126 |
|  | REPS | 30 | 18 | 174 | 174 | 177 | 145 | 74 | 69 | 159 |
|  | DIFF | 2 | 1 | 6.7 | 4 | 5 | 2 | 3 | 18 | 0 |
|  | PROB | .000# | .001# | .000# | .001# | .000# | .103 | .023+ | .000# | .061* |

| DEPT | VAR # | GRN APP % MN | SDG VGR % MN | EST CNT % MN | STK CNT % MN | PLT HT % MN | EAR HT % MN | DRP EAR % MN | BRT STK % MN | GDU SHD % MN |
|---|---|---|---|---|---|---|---|---|---|---|
| TOTAL SUM | 1 | 102 | 103 | 98 | 100 | 103 | 92 | 100 | 102 | 100 |
|  | 2 | 91 | 103 | 100 | 100 | 95 | 85 | 100 | 102 | 98 |
|  | LOCS | 45 | 51 | 87 | 145 | 70 | 70 | 50 | 7 | 50 |
|  | REPS | 55 | 72 | 107 | 189 | 82 | 82 | 68 | 10 | 60 |
|  | DIFF | 11 | 0 | 2 | 0 | 8 | 7 | 0 | 0 | 2 |
|  | PROB | .000# | .940 | .064* | .684 | .000# | .000# | .170 | .885 | .000# |

* = 10% SIG
+ = 5% SIG
# = 1% SIG

TABLE 5B

VARIETY #1 - PHHB4 HYBRID
VARIETY #2 - PHR61 HYBRID

| DEPT | VAR # | PRM | PRM SHD | BU ACR ABS | BU ACR % MN | MST % MN | STK LDG % MN | RT LDG % MN | STA GRN % MN | TST WTA % MN |
|---|---|---|---|---|---|---|---|---|---|---|
| TOTAL SUM | 1 | 107 | 108 | 178.7 | 105 | 97 | 98 | 100 | 90 | 100 |
|  | 2 | 103 | 107 | 165.0 | 98 | 88 | 100 | 103 | 85 | 102 |
|  | LOCS | 23 | 15 | 105 | 105 | 105 | 87 | 43 | 43 | 95 |
|  | REPS | 23 | 15 | 137 | 137 | 137 | 110 | 58 | 54 | 119 |
|  | DIFF | 4 | 1 | 13.7 | 8 | 9 | 2 | 3 | 4 | 2 |
|  | PROB | .000# | .005# | .000# | .000# | .000# | .175 | .363 | .512 | .000# |

| DEPT | VAR # | GRN APP % MN | SDG VGR % MN | EST CNT % MN | STK CNT % MN | PLT HT % MN | EAR HT % MN | DRP EAR % MN | BRT STK % MN | GDU SHD % MN |
|---|---|---|---|---|---|---|---|---|---|---|
| TOTAL SUM | 1 | 103 | 100 | 98 | 100 | 104 | 93 | 100 | 102 | 101 |
|  | 2 | 107 | 103 | 102 | 101 | 103 | 97 | 100 | 102 | 100 |
|  | LOCS | 41 | 36 | 64 | 107 | 49 | 49 | 34 | 7 | 33 |
|  | REPS | 50 | 53 | 80 | 142 | 56 | 56 | 47 | 10 | 38 |
|  | DIFF | 4 | 4 | 4 | 1 | 1 | 4 | 0 | 0 | 1 |
|  | PROB | .137 | .415 | .000# | .220 | .338 | .013+ | .243 | .939 | .000# |

\* = 10% SIG
\+ = 5% SIG
\# = 1% SIG

INDUSTRIAL APPLICABILITY

The foregoing is set forth by way of example and is not intended to limit the scope of the invention.

This invention also is directed to methods for producing a corn plant by crossing a first parent corn plant with a second parent corn plant wherein the first or second parent corn plant is an inbred corn plant from the line PHHB4. Further, both first and second parent corn plants can come from the inbred corn line PHHB4. Thus, any such methods using the inbred corn line PHHB4 are part of this invention: selfing, backcrosses, hybrid production, crosses to populations, and the like. It also would include more unconventional methods of combining the inbred with another such as using various culturing techniques known to those skilled in the art. All plants produced using inbred corn line PHHB4 as a parent are within the scope of this invention. Advantageously, the inbred corn line is used in crosses with other, different, corn inbreds to produce first generation ($F_1$) corn hybrid seeds and plants with superior characteristics.

As used herein, the term plant includes plant cells, plant protoplasts, plant cell tissue cultures from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

Duncan, Williams, Zehr, and Widholm, *Planta*, (1985) 165:322-332 reflects that 97% of the plants cultured which produced callus were capable of plant regeneration. Subsequent experiments with both inbreds and hybrids produced 91% regenerable callus which produced plants. In a further study in 1988, Songstad, Duncan & Widholm in *Plant Cell Reports* (1988), 7:262-265 reports several media additions which enhance regenerability of callus of two inbred lines. Other published reports also indicated that "nontraditional" tissues are capable of producing somatic embryogenesis and plant regeneration. K. P. Rao, et al., *Maize Genetics Cooperation Newsletter*, 60:64-65 (1986), refers to somatic embryogenesis from glume callus cultures and B. V. Conger, et al., *Plant Cell Reports*, 6:345-347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of corn is described in European Patent Application, publication 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottesville, Va. 1982, at 367-372) and in Duncan, et al., "The Production of Callus Capable of Plant Regeneration from Immature Embryos of Numerous Zea Mays Genotypes," 165 *Planta* 322-332 (1985). Thus, another aspect of this invention is to provide cells which upon growth and differentiation produce corn plants having the physiological and morphological characteristics of the inbred line PHHB4.

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide corn starch, corn syrups, and dextrose for food use. Corn oil is recovered from corn germ, which is a by-product of both dry- and wet-milling industries.

Corn, including both grain and non-grain portions of the plant, is also used extensively as livestock feed, primarily for beef cattle, dairy cattle, hogs, and poultry.

Industrial uses of corn are mainly from corn starch in the wet-milling industry and corn flour in the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel and to make charcoal.

The seed of inbred corn line PHHB4, the plant produced from the inbred seed, the hybrid corn plant produced from the crossing of the inbred, hybrid seed, and various parts of the hybrid corn plant can be utilized for human food, livestock feed, and as a raw material in industry.

Although the foregoing invention has been described in some detail by way of illustration and example for the purposes of clarity and understanding, it will be obvious that certain changes and modifications may be practiced within the scope of the invention, as limited only by the scope of the appended claims.

Deposits

Applicant has made a deposit of at least 2500 seeds of Inbred Corn Line PHHB4 with the American Type Culture Collection (ATCC), Rockville, Md. 20852 USA, ATCC Deposit No. 97048. The seeds deposited with the ATCC on Feb. 9, 1995 were taken from the deposit maintained by Pioneer Hi-Bred International, Inc., 700 Capital Square, 400 Locust Street, Des Moines, Iowa 50309-2340 since prior to the filing date of this application. The deposit of the Inbred Corn Line PHHB4 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has satisfied all the requirements of 27 C.F.R. §§1.801–1.809, including providing an indication of the viability of the sample. Applicant imposes no restrictions on the availability of the deposited material from the ATCC; however, Applicant has no authority to waive any restrictions imposed by law on the transfer of biological material or its transportation in commerce. Applicant does not waive any infringement of its rights granted under this patent or under the Plant Variety Protection Act (7 USC 2312 et seq.). PHHB4 is a U.S. protected variety under Plant Variety Protection Certificate 9400093.

What is claimed is:

1. Parts of a plant produced by a seed designated PHHB4 and having ATCC accession number 97048.

2. Parts of a $F_1$ hybrid corn plant grown from a $F_1$ hybrid corn seed produced by crossing inbred corn plant PHHB4, having ATCC accession number 97048, with another corn plant that is not PHHB4.

* * * * *

UNITED STATES PATENT AND TRADEMARK OFFICE
CERTIFICATE OF CORRECTION

PATENT NO. : 5,633,427
DATED : May 27, 1997
INVENTOR(S) : Stephen W. Noble, Jr.

It is certified that error appears in the above-indentified patent and that said Letters Patent is hereby corrected as shown below:

On the title page:

[54] INBRED CORN LINE PHHB please change to --INBRED CORN LINE PHHB4--

Column 1, line 1:

please change to--INBRED CORN LINE PHHB4--

Signed and Sealed this

Twenty-first Day of October 1997

Attest:

BRUCE LEHMAN

*Attesting Officer*  *Commissioner of Patents and Trademarks*